US007332354B2

United States Patent
Heindl et al.

(10) Patent No.: US 7,332,354 B2
(45) Date of Patent: Feb. 19, 2008

(54) COMPOUNDS FOR CHEMILUMINESCENSE PROCEDURES

(75) Inventors: Dieter Heindl, Paehl (DE); Rupert Herrmann, Weilheim (DE); Hans-Peter Josel, Weilheim (DE); Erasmus Huber, Finning (DE); Ursula Klause, Peissenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 522 days.

(21) Appl. No.: 10/479,320

(22) PCT Filed: May 28, 2002

(86) PCT No.: PCT/EP02/05855

§ 371 (c)(1),
(2), (4) Date: Jun. 14, 2004

(87) PCT Pub. No.: WO02/099097

PCT Pub. Date: Dec. 12, 2002

(65) Prior Publication Data

US 2004/0214999 A1    Oct. 28, 2004

(30) Foreign Application Priority Data

Jun. 1, 2001    (EP)    ................... 01112879

(51) Int. Cl.
*G01N 33/532* (2006.01)
*G01N 33/533* (2006.01)
*C12P 7/40* (2006.01)
*C07D 219/00* (2006.01)
*C07D 277/62* (2006.01)

(52) U.S. Cl. .............. 436/544; 436/546; 436/800; 436/904; 435/136; 435/968; 546/102; 548/178

(58) Field of Classification Search ................ 436/544, 436/546, 800, 904; 435/136, 968; 546/102; 548/178

See application file for complete search history.

(56) References Cited

U.S. PATENT DOCUMENTS 5,098,828 A * 3/1992 Geiger et al. ............. 435/7.72
5,589,328 A    12/1996 Mahant
5,593,845 A    1/1997 Akhavan-Tafti et al.
5,669,819 A    9/1997 Mattingly et al.

FOREIGN PATENT DOCUMENTS

| EP | 0 510 668 A2 | 10/1992 |
|---|---|---|
| EP | 0 625 510 A3 | 11/1994 |
| WO | WO 95/19976 | 7/1995 |
| WO | WO 97/33884 | 9/1997 |
| WO | WO 98/56765 | 12/1998 |
| WO | WO 01/09372 A1 | 2/2001 |
| WO | WO 92/09580 | 6/2002 |

OTHER PUBLICATIONS

Hunig, Siegfried, Aromatic/quinoid systems: principles and applications. Pure & App. Chem. vol. 62, No. 3, pp. 395-406, 1990.
Mayer, A, Neuenhofer, S. Luminescen Labels—More than Just an Alternative to Radioisotopes?, Angew. Chem. Int. Ed. Engl. 1994, 33, 1044-1072.
Waldrop III, A., Fellers, J., Vary C.P. "Chemiluminescent determination of hydrogen peroxide with 9-acridinecarbonylimidazole and use in measurement of glucose oxidase and alkaline phosphatase activity", Luminescence 2000;15: 169-182.

* cited by examiner

*Primary Examiner*—Long V. Le
*Assistant Examiner*—Shafiqul Haq
(74) *Attorney, Agent, or Firm*—Marilyn L. Amick; Roche Diagnostics Operations, Inc.

(57) ABSTRACT

The present invention relates to a chemical compound comprising a light emitting moiety precursor and a precursor of a leaving group, bound to each other by an amide or by an ester bond and characterized in that the leaving group precursor upon oxidation is converted into the leaving group. The invention also relates to compounds additionally comprising a coupling group to the use of such compounds for labeling of biomolecules and more generally to the use of such compounds in chemiluminescence detection procedures.

4 Claims, 7 Drawing Sheets

Acridinium ester: Postulated reaction mechanism

Schematic of an acridinium-9-(N-sulfonyl) carboxamide label

Reaction kinetics of an acridinium-oxazine

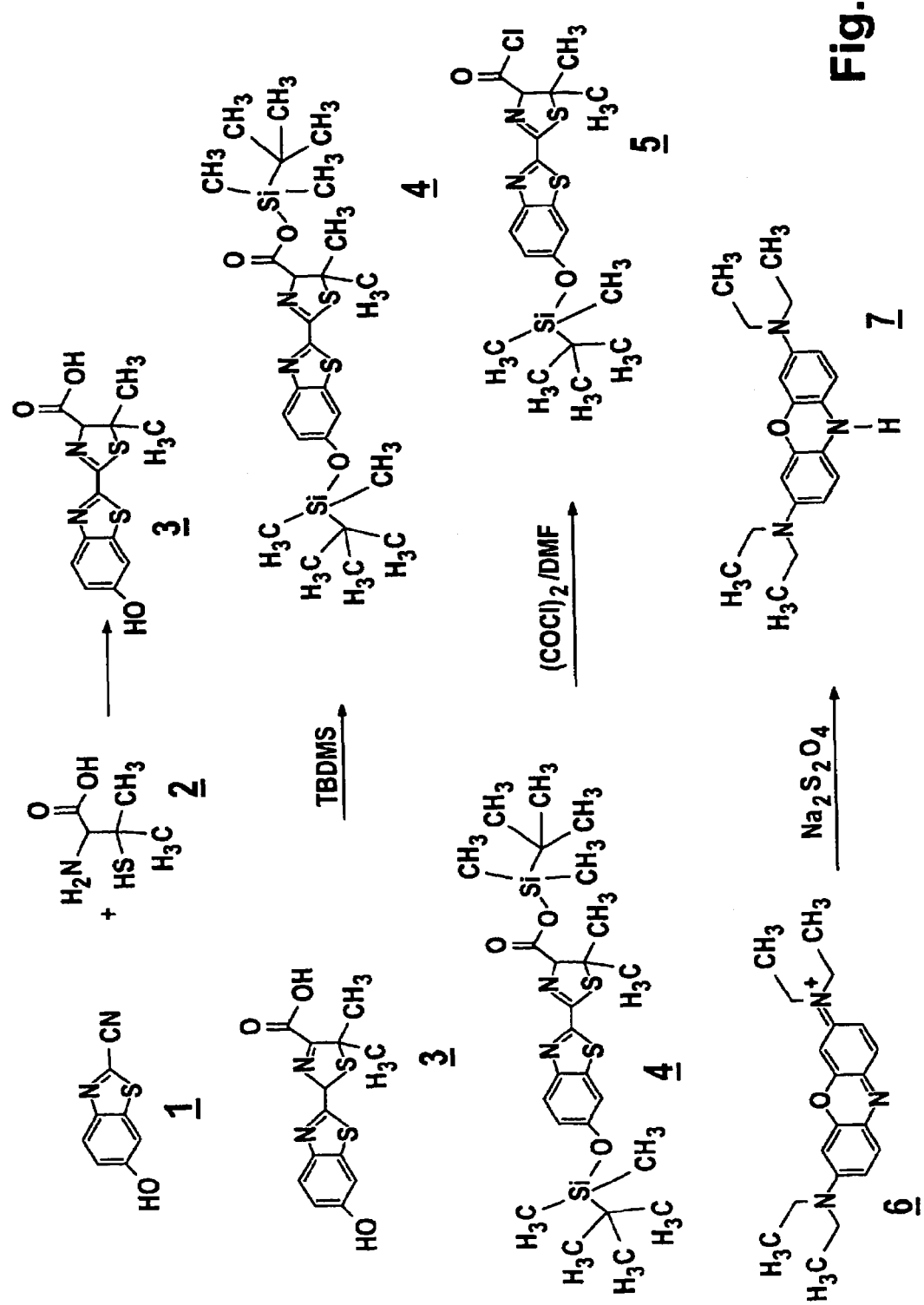
Fig. 6/1

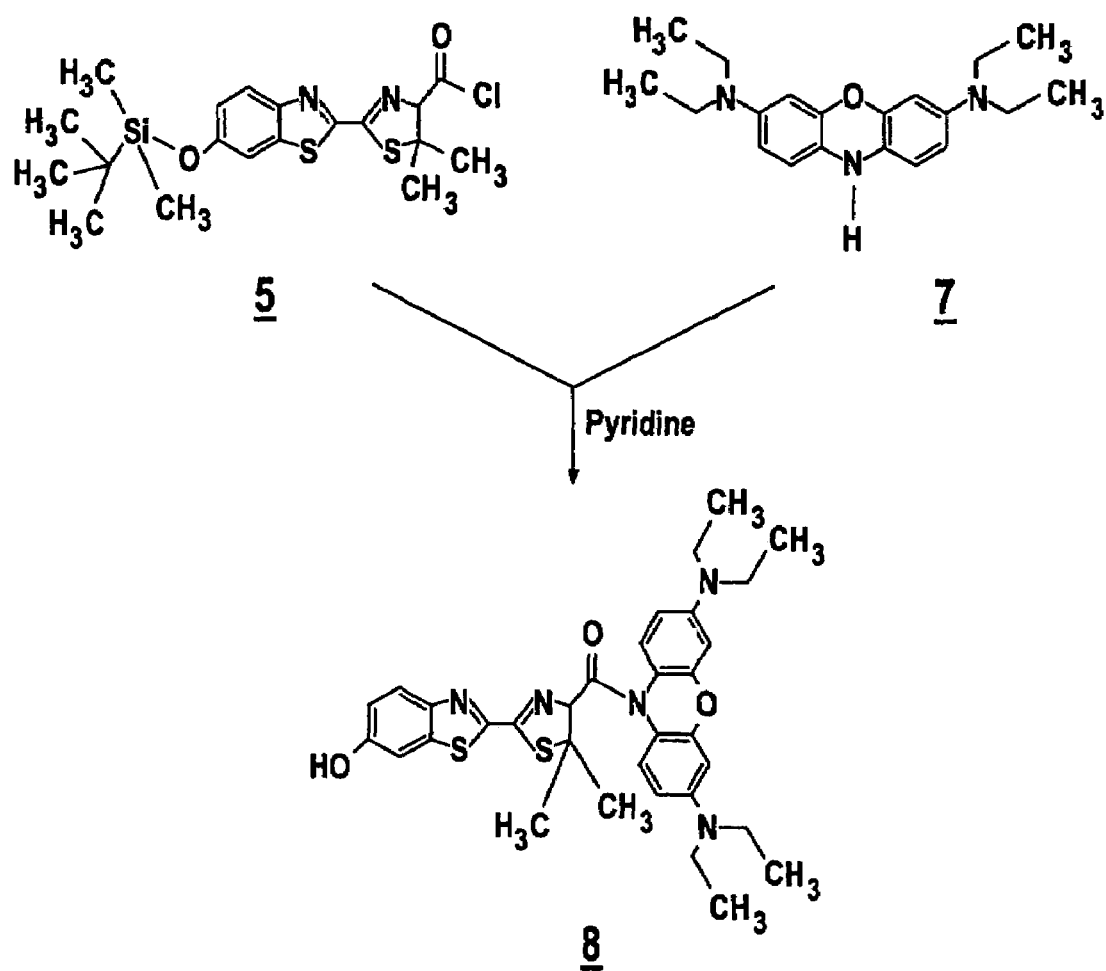
Synthesis pathway for a luciferin-benzoxazine compound
Fig. 6/2

COMPOUNDS FOR CHEMILUMINESCENSE PROCEDURES

The present invention relates to a chemical compound comprising a light emitting moiety precursor and a precursor of a leaving group, bound to each other by an amide or by an ester bond and characterized in that the leaving group precursor upon oxidation is converted into the leaving group. The invention also relates to compounds additionally comprising a coupling group to the use of such compounds for labeling of biomolecules and more generally to the use of such compounds in chemiluminescence detection procedures.

The specific detection and quantitation of biological molecules has been accomplished with excellent sensitivity for example by the use of radio-labeled reporter molecules. The first radio immunoassays developed in the end of the 1950's have matured into the most important tools of in vitro diagnostics, especially in medicine, using a broad variety of different detection or reporter systems. Well-known examples of reporter molecules are enzymes, labeled latex beads, fluorescent dyes and especially chemiluminescent dyes. Reviews describing the theory and practice of specific binding assays are available.

The skilled artisan will find all necessary technical details for performing specific binding assays in textbooks like "Practice and theory of enzyme immunoassays" Tijssen (1990) Amsterdam, Elsevier and various editions of "Methods in Enzymology" Colowick, S. P. and Caplan, N. O. (1980-1986), Academic Press, dealing with immunological detection methods, especially volumes 70, 73, 74, 84, 92 and 121.

Paralleled by the development of light measuring techniques and the commercial availability of highly sensitive apparatus, luminophores have in many applications replaced isotopic labels. Some of the new luminescent labels facilitate analyte detection at extremely low levels of sensitivity. Therefore such labels also commercially are very interesting.

Luminescent labels may be subdivided into the group of fluorescent labels and the group of luminescent labels. Whereas fluorescent labels require irradiation of a sample with excitation light in order to detect and measure the fluorescent label present, the chemiluminescent systems do not require an extra source of light.

Well known chemiluminescent based systems make use of labels comprising amongst others the following categories, the combination of luciferins with corresponding luciferases, cyclic arylhydrazides, acridinium derivatives, stable dioxetanes, and oxalic acid derivatives.

Some of the developments achieved as well as of problems still encountered in the art shall be exemplified by discussing one specific example, the acridinium esters.

Acridinium esters represent a very important class of compounds used in chemiluminescence. An essential feature of such an acridinium ester is that the ester function has been substituted to carry a suitable leaving group. Suitable leaving groups are designed to match as good as possible two essential requirements: stability and high quantum yield.

On the one hand the leaving group of an acridinium esters must be as active as possible, i.e., leaving quite readily under measurement conditions, to allow for a sensitive detection and high quantum yield. This high activity on the other hand, however, goes to the expense of instability towards hydrolysis. Such instabilities are even more critical if such chemiluminescent labels are used for conjugation to biomolecules. The goal to achieve a high chemiluminescent yield and in addition a high stability of the labeled reagent equals to a fine balance act always ending in a compromise between light yield and stability.

To at least partially solve the problems encountered, new and different leaving groups have been designed. Most popular are N-sulfonamides, e.g., described in U.S. Pat. No. 5,669,819, thioesters as described in DE 3 645 292, hydroxamic acid esters described in WO 98/56765, imidazolides as described by Waldrop III, A. A., et al., Luminescence 15 (2000) 169-182, and pyridinium amides (WO 95/19976).

Some chemicals comprising an acridinium or an acridan dye and a phenol or hydroxy-phenol group bound by ester bond are known from a different field of research. These acridinium or acridan ester have been used as enzyme substrates or the phenol group has been described to modulate the hydrolytic stability or lability, respectively, of the ester bond (WO 97/33884; WO 01/09372; EP 625 510).

Another approach has been the use of acridan compounds (U.S. Pat. No. 5,593,845) which after oxidation of the acridan moiety act similarly as compared to acridinium dyes. However, all alternatives described contain an active ester moiety which still is subject to hydrolysis and requires careful and special storage as well as handling conditions.

It was the task of the present invention to find and identify novel dye compounds for chemiluminescence assays which provide for a stable chemiluminescent dye or label on the one hand and for sensitive detection or high quantum yield on the other hand. Especially compounds additionally comprising a coupling group are needed which are suitable for labeling of, or conjugation to a biomolecule.

Surprisingly, it has been found that compounds can be synthesized comprising a light emitting moiety precursor and a precursor of a leaving group which help to overcome problems known in the art. These novel compounds comprise a stable amide bond between a nitrogen atom of the leaving group precursor and a carbonyl group of a light emitting moiety precursor, wherein this nitrogen atom is part of a redox system or they comprise a stable ester bond between an oxygen atom of the leaving group precursor and a carbonyl group of the light emitting group precursor, wherein this oxygen is part of a redox system.

After oxidation of the leaving group precursor the amide bond or the ester bond becomes activated and the light emitting group precursor is ready to generate chemiluminescence after reaction with peroxide.

In summary the present invention relates to a chemical compound comprising a light emitting moiety precursor and a precursor of a leaving group, wherein a carbonyl group of said light emitting moiety precursor is linked via amide bond or via ester bond to the leaving group precursor, characterized in that said leaving group precursor upon oxidation is converted into a leaving group.

The invention also relates to compounds comprising a light emitting moiety precursor, a precursor of a leaving group and a coupling group.

Since the compounds according to the present invention encompass both storage stability, as well as sensitive detection in chemiluminescent procedures they are also used to label biomolecules and the resulting conjugates with great advantage can be applied in appropriate specific binding assays for detection of an analyte in a sample.

With great advantage the novel compounds can be used in the detection of peroxide as well as in the detection of peroxidase.

The invention also relates to a method of performing a chemiluminescence measurement using a novel compound as described in which method the leaving group precursor first is oxidized, the light emitting group precursor becomes reactive, energy in form of light is generated according to standard procedures and the emitted light is measured as usual.

DETAILED DESCRIPTION OF THE INVENTION

The present invention relates to a chemical compound comprising a light emitting moiety precursor and a precursor of a leaving group, wherein a carbonyl group or a chemically equivalent group of said light emitting moiety precursor is linked via amide bond to a nitrogen atom of the leaving group precursor which is characterized in that said leaving group precursor upon oxidation is converted into the leaving group.

The present invention also relates to a chemical compound comprising luciferin as a light emitting moiety precursor and a precursor of a leaving group, wherein a carbonyl group or a chemically equivalent group of said luciferin is linked via ester bond to an oxygen atom of the leaving group precursor, characterized in that said leaving group precursor upon oxidation is converted into the leaving group.

The chemical compounds according to the present invention comprise a light emitting moiety precursor and a precursor of a leaving group. These two chemical entities are linked together via an amide or an ester bond. This amide or this ester bond, respectively, is stable thus ensuring the stability of the overall chemical structure. This rather stable bond, e.g., is not hydrolyzed under physiological conditions or under routine storage conditions. The chemical compound according to the present invention may also be described as a derivative of a light emitting moiety. These novel derivatives of a light emitting moiety can be easily handled, e.g., during conjugation to biomolecules or under long-term storage conditions, e.g. as required for many commercial applications.

A "light emitting moiety precursor" in the sense of the present invention comprises such chemical moieties, which upon appropriate activation can be used and measured in an analysis system based on the detection of chemiluminescence. Well-known classes of chemical compounds used in chemiluminescent labeling comprise amongst others luciferins in combination with the corresponding luciferases, cyclic arylhydrazides, acridinium derivatives, stable dioxetanes, and oxalic acid derivatives.

The light emitting moiety precursor of the present invention must carry a carbonyl group or a chemically equivalent group. In a compound according to the present invention, the light emitting moiety precursor, of course, is not present as a free light emitting group precursor but rather it comprises an amide or ester of the leaving group precursor. With other words the light emitting moiety precursor in the compounds described has to be understood as the carboxylic acid part of an ester or amide of the free light emitting group precursor.

The characteristic and important function of the carbonyl group is that nucleophils, like $H_2O_2$, can attack the $sp^2$ carbon atom. It is well-known that groups like thiocarbonyls or cyanimino residues bring about similar chemical properties. Amongst these groups carbonyl groups are preferred. In order to avoid linguistic redundancies, in the following in most cases simply the term carbonyl group is used. It has to be understood, however, that appropriate functional equivalents may as well be used.

By oxidation the leaving group precursor is converted into the leaving group, and as the term indicates, leaves after reaction of the carbonyl group with peroxide.

The carbonyl group which is part of the stable amide or ester bond is the same carbonyl function which (after the leaving group has been formed) upon attack by peroxide and accompanied by emission of light is cleaved off from the light emitting moiety precursor.

One preferred class of chemiluminescence labels are the acridinium compounds. Their mechanism of chemiluminescence has been extensively studied and is nicely summarized in a review article published in "Angewandte Chem. Intern. Ed. Engl.", by Mayer, A. and Neuenhofer, S. (1994) 1044-1072, Weinheim, VCH Verlagsgesellschaft mbH.

Several mechanisms leading to emission of light according to the chemiluminescence principles have been proposed. Short-lived intermediates are considered part of the processes leading to decarboxylation and emission of light. The processes postulated for acridinium ester labels, resulting in emission of light or in the unwanted side reaction (dark reaction) leading to hydrolysis of the ester, are schematically shown in FIG. 1.

According to the proposed mechanism the carbonyl group (which has been part of the amide or ester bond) by attack of $H_2O_2$ becomes part of a dioxetanone moiety. Spontaneous decomposition of the dioxetanone moiety is accompanied by light emission and yields a heterocyclic ketone and $CO_2$ in case of a carbonyl group, or in more general chemical terms a heterocumulene in case functional equivalents of the carbonyl group had been present.

It is instantly evident from FIG. 1, that the light reaction (LR) and the dark processes (DP) both are dependent on the properties of the leaving group Z. Quite different to the compounds known in the art and as illustrated in FIG. 1, in a compound according to the present invention, instead of a leaving group Z a precursor of a leaving group is present.

The term "precursor of a leaving group" is used to indicate that without further chemical modification, according to the present invention oxidation, the leaving group precursor will not function as leaving group or at least is rather a poor leaving group and no light emitting moiety precursor will be set free. Without oxidation of the aromatic system of the leaving group precursor the amide bond between the light emitting moiety precursor and the leaving group precursor is stable towards hydrolysis.

Only at a first glance the so-called acridinium-9-(N-sulfonyl)carboxamide labels structurally appear to be similar to the compounds according to the present invention. An example of such label is shown in FIG. 2. Chemically, however, the acridinium-9-(N-sulfonyl)carboxamide labels are quite different to the compounds according to the present invention. The nitrogen atom—due to the neighboring —$SO_2$ group—chemically spoken is an electron poor nitrogen and not part of an oxidizable aromatic or redox system, otherwise it would not function as a leaving group. These properties of the nitrogen atom are especially brought about the N-sulfonylamide group linked to it. As for all chemiluminescent labels known in the art these acridinium-9-(N-sulfonyl)carboxamide labels represent a compromise between stability of a chemiluminescent label towards hydrolysis and fast and efficient release of the leaving group for sensitive detection.

In the compounds according to the present invention precursors of a leaving group are used instead of a leaving group, precursors, which are characterized in that they contain an "oxidizable" nitrogen within an amide bond which is also part of an aromatic system or an "oxidizable" oxygen atom of an ester bond.

"Oxidizable" means that said nitrogen or oxygen atom is electron rich and that electrons can be readily withdrawn, i.e. that nitrogen or that oxygen thus is oxidized. As the skilled artisan will appreciate, an electron rich oxygen or nitrogen requires the attachment of at least one so-called (electron) donor substituent. Electron donor substituents are well-known to the skilled artisan and need not to be detained here. The donor substituent can be attached directly or alternatively vinylogous or phenylogous to the nitrogen or oxygen atom. In both cases the nitrogen or oxygen atom is part of the reduced form of a two step donor-pi-donor redox system, also known as reversible two step redox system, as described by Huenig (Huenig S., Pure Appl Chem, 62 (1990) 395-406).

Oxidizable nitrogen atoms of appropriate aromatic systems are well-known in the art. The most popular oxidizable aromatic systems are leuko-dyes, which upon oxidation are converted into dyes. In these aromatic leuko-dye/dye-systems the electron-rich nitrogen of the leuko-dye upon oxidation is converted into an electron poor nitrogen. This oxidation renders the amide bond highly unstable and the oxidized form of such leaving group precursor now efficiently works as leaving group.

In a preferred embodiment the chemical compound according to the present invention is a compound according to formula 1.

Formula 1:

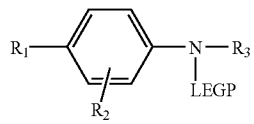

Wherein,
$R^1$=—$NR^3R^4$, —$OR^5$, —$SR^6$, —$NR^7NR^3R^4$
$R^2$=H, $R^1$, ($C_1$-$C_{10}$)-alkyl, $C_2$-$C_{10}$ alkenyl, $C_2$-$C_{10}$ alkynyl, $C_6$-$C_{22}$ aryl, $SO_3^-$, —COOH, -halogen, nitro, anellated benzene,
$R^3$ to $R^7$=H, ($C_1$-$C_{10}$)-alkyl, $C_2$-$C_{10}$ alkenyl, $C_2$-$C_{10}$ alkynyl, $C_6$-$C_{22}$ aryl;
wherein any alkyl, alkenyl, alkynyl or aryl can be substituted by one or more moieties selected from the group consisting of -halogen, a coupling group, —$OPO_3^{2-}$, $PO_3^{2-}$, —$SO_3^-$, —$COOR^5$, —CO—$NR^3R^4$, —S—$R^6$, —$NR^3R^4$, —$N^+(C_1$-$C_6Alkyl)_3$, —$OR^5$, —$COR^5$, —NH—CO—$NR^3R^4$, —NH—CS—$NR^3R^4$, and —$(CH_2)_n$—[O—$(CH_2)_r]_s$—$NR^3R^4$, —$(CH_2)_n$—[O—$(CH_2)_r]_s$—$OR^5$ wherein r and s are independently of each other an integer of from 1 to 18 and n is 0 or 1 independently from r and s; and wherein
LEGP stands for light emitting group precursor.

Preferably R1 is —$NR^3R^4$ or —$OR^5$, wherein $R^3$ to $R^5$ independently is H, ($C_1$-$C_1$)-alkyl or an ($C_1$-$C_{10}$)-alkyl substituted by a coupling group. Most preferred R1 is —N(-ethyl)$_2$, —O-ethyl, N(-methyl)$_2$, O-methyl or one of these residues substituted by a coupling group.
$R^2$ preferably is H or -methyl.

In a further preferred embodiment the compound according to the present invention is represented by Formula 2.

Formula 2:

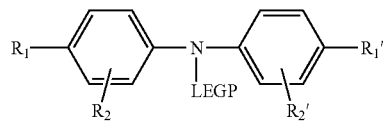

Wherein,
$R_1$ and $R_1'$ independently are residues as defined above for $R_1$,
$R_2$ and $R_2'$ are independently residues as defined above for $R^2$, and LEGP is the light emitting group precursor.

In a further preferred embodiment the leaving group precursor comprises the structural elements as summarized in formula 3.

Formula 3:

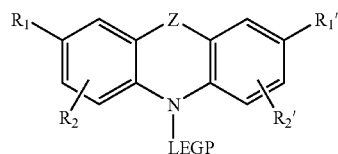

Wherein,
$R_1$ and $R_1'$ independently are residues as defined above for $R_1$,
$R_2$ and $R_2'$ are independently residues as defined above for $R^2$, LEGP is the light emitting group precursor, and
Z represents S, O, or N—$R^8$, and wherein $R^8$ is H, ($C_1$-$C_{10}$)-alkyl, $C_2$-$C_{10}$ alkenyl, $C_2$-$C_{10}$ alkynyl, $C_6$-$C_{22}$ aryl.

In all the structures summarized in Formulas 1-3, the nitrogen atom is part of a redox system, preferably of an oxidizable aromatic system. This structural feature, i.e., the nitrogen atom of the leaving group precursor being part of redox system represents a preferred embodiment according to the present invention. Upon oxidation the nitrogen of the leaving group precursor is oxidized as part of this redox system. The amide bond between the light emitting group precursor and the oxidized nitrogen is chemically very unstable and the light emitting group precursor is readily released upon reaction with $H_2O_2$.

In a preferred embodiment the leaving group precursor is a leuko-dye. More preferred such leuko-dye can be represented by structures comprised in formula 3. It is preferred to select the leaving group from the leuko-dyes corresponding to the classes of chemical substances consisting of resorufine, oxazine and methylene blue.

In a preferred embodiment the light emitting moiety precursor comprises a chemiluminogenic heterocycle. Examples of such chemiluminogenic heterocycles are well-known in the art and e.g. summarized in the review article by Mayer, A. and Neuenhofer, S. in "Angewandte Chem. Intern. Ed. Engl." (1994) 1044-1072, Weinheim, VCH Verlagsgesellschaft mbH.

As described further above the light emitting moiety precursor is selected from compounds containing a carbonyl group or a chemically equivalent functional group to which the leaving group precursor is bound by amide bond. Preferably the light emitting moiety (or group) precursor is selected from the following categories of chemiluminescent compounds: 4Hbenzo[e] [1,3]oxazine, 4,5-dihydrothiazole, luciferin, acridan and acridinium dyes. Of course, the signal or light emitting moiety precursor according to the invention is not restricted to the dyes themselves but also includes chemiluminescent derivatives thereof.

In the chemical compound comprising a light emitting moiety precursor and a precursor of a leaving group, wherein a carbonyl group or a chemically equivalent group of said light emitting moiety precursor is linked via an amide bond to a nitrogen atom of the leaving group precursor the light emitting group precursor preferably is a chemiluminogenic heterocycle, which is selected from the group consisting of luciferin, acridinium and acridan.

In a preferred embodiment the present invention relates to a chemical compound comprising luciferin or an analogue thereof as a light emitting moiety precursor and a precursor of a leaving group, wherein a carbonyl group or a chemically equivalent group of said luciferin is linked via amide bond to a nitrogen atom of the leaving group precursor, characterized in that said leaving group precursor upon oxidation is converted into the leaving group.

In a further preferred embodiment the light emitting precursor and the leaving group precursor are linked by an ester bond.

Examples for such compounds are represented by the general formulas 4 and 5.

Formula 4:

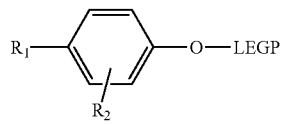

Formula 5:

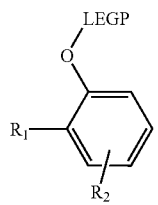

Wherein, $R_1$ and $R_2$ represent residues as defined above and LEGP is the light emitting group precursor.

The oxygen atom of this ester bond is part of a redox system. Appropriate groups rendering the oxygen atom oxidizable are electron donating groups like —$OR^5$, —$SR^6$, —$NR^3R^4$ or —$NR^7$—$NR^3R^4$ (wherein $R^3$ to $R^7$ are as defined above) in ortho- or para-position of the phenol residue. Upon oxidation the ester bond becomes highly unstable. With other words, the leaving group precursor is converted into the leaving group.

In a preferred embodiment the leaving group precursor which is bound to the light emitting moiety precursor by ester bond is selected from the group comprising phenoles substituted with an electron donor group in ortho- or para-position. Most preferred electron donors are —$NR^3R^4$ or —O—$R^5$, wherein R preferably is —H or $C_1$ to $C_5$ alkyl.

The light emitting group precursor, in formula 4 and formula 5 is a luciferin (Formula 6) or an analogue thereto (e.g., Formula 7 or Formula 8).

Formula 6:

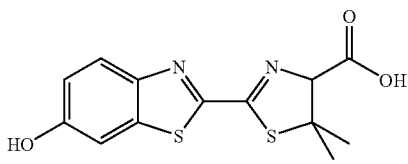

Formula 7:

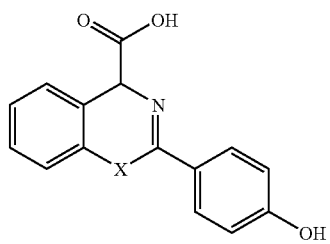

X=O 2-(4 hydroxyphenyl) 4H benzo[e] [1,3] oxazine-4-carboxylic acid

X=S 2-(4 hydroxyphenyl)4H benzo[e] [1,3] thiazine-4-carboxylic acid

X=N-alkyl N-alkyl-2-(4 hydroxyphenyl) 1,4 dihydro quinazolin 4-carboxylic acid

Formula 8:

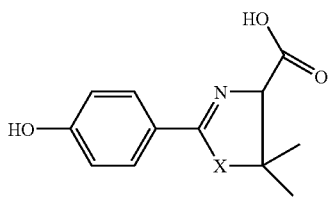

X=O 2-(4 hydroxyphenyl) 4,5 dihydro oxazole 5,5 dimethyl-4-carboxylic acid

X=S 2-(4 hydroxyphenyl) 4,5 dihydro thiazole 5,5 dimethyl-4-carboxylic acid

X=N-alkyl N-alkyl-2-(4 hydroxyphenyl) 4,5 dihydro imidazol 5,5 dimethyl-4-carboxylic acid.

In a preferred embodiment the present invention therefore relates to a chemical compound comprising luciferin as a light emitting moiety precursor and a precursor of a leaving group, wherein a carbonyl group or a chemically equivalent group of said luciferin is linked via ester bond to an oxygen atom of the leaving group precursor, characterized in that said leaving group precursor upon oxidation is converted into the leaving group.

It is further preferred that in case of an oxidizable ester bond between luciferin or an analogue thereto and a leaving group precursors said leaving group precursor is selected from the group consisting of leuko-resorufin, and a phenol group substituted with an electron donor group in ortho- or para-position. Most preferred the leaving group is a phenol group substituted with an electron donor group in ortho- or para-position.

In a further preferred embodiment the chemical compound according to the present invention comprises two light emitting group precursors. The LEGP may be identical, however, it is also possible to use two different LEGPs. Each of these light emitting group precursors is linked to a leaving group precursor by a stable but oxidizable amide or ester bond. Preferably both bonds between the leaving group precursor and the light emitting group precursors are of the same type. However, in special settings, e.g. where different redox systems are applied, structures comprising two different types of bond, e.g., an ester bond or an amide bond may be advantageous.

In compounds comprising two light emitting group precursors the leaving group precursor preferably is a substituted phenol group. Most preferred the two light emitting group precursors are attached to this phenol group in para-position.

Examples of structures comprising two light emitting group precursors are given in formulas 9, 10, and 11.

Formula 9:

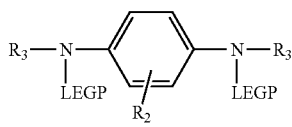

Formula 10:

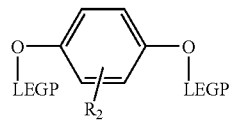

Formula 11:

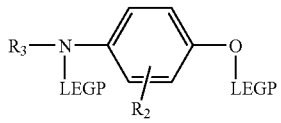

In Formula 9 to Formula 11 $R_2$ and $R_3$ represent residues as defined above and LEGP is a light emitting group precursor The compounds according to the present invention comprising a light emitting moiety precursor and a precursor of a leaving group represent very attractive labels, e.g., for labeling of biomolecules. The methods used for coupling of labels to biomolecules have significantly matured during the past years and an excellent overview is given in "Bioconjugation" Aslam, M. and Dent, A. (1998) 216-363, London, McMillan Reference and in the chapter "Macromolecule conjugation" in "Practice and theory of enzyme immunoassays" Tijssen (1990), Elsevier, Amsterdam.

Appropriate coupling chemistries are known from the above cited literature (Aslam, supra). The chemical compound according to the present invention preferably is designed and synthesized to comprise a coupling group which matches the coupling chemistry appropriate for the biomolecule under investigation.

In a preferred embodiment the chemical compound according to the present invention comprises a light emitting moiety precursor, a precursor of a leaving group and a coupling group, wherein a carbonyl group or a chemically equivalent group of said light emitting moiety precursor is linked via amide bond to a nitrogen atom of the leaving group precursor, characterized in that said leaving group precursor upon oxidation is converted into the leaving group.

In a further preferred embodiment the chemical compound, comprises luciferin or an analogue thereto as a light emitting moiety precursor, a precursor of a leaving group and a coupling group, wherein a carbonyl group or a chemically equivalent group of said light emitting moiety precursor is linked via ester bond to an oxygen atom of the leaving group precursor, characterized in that said leaving group precursor upon oxidation is converted into the leaving group.

The chemical compound according to the present invention thus preferably also contains a coupling group, which may be termed Y. The coupling group Y is a reactive group or activated group which is used for chemically coupling of the compound to a biomolecule. The group Y preferably is an activated carboxylic acid group such as a carboxylic acid halogenide, a carboxylic acid anhydride, a carboxylic acid hydrazide, a carboxylic acid azide or an active ester e.g. an N-hydroxy-succinimide, a p-nitrophenyl, pentafluorophenyl, imidazolyl or N-hydroxybenzotriazolyl ester, an amine, a maleimide, a thiol, a para-aminobenzoyl group or a photoactivatable group e.g. an azide. Most preferred Y is an N-hydroxy-succinimide ester.

The coupling group Y is selected to match the chemical function on the biomolecule to which coupling shall be performed.

Amino groups of biomolecules (the terminal —$NH_2$ group or the $NH_2$ group of a lysine side chain, as well as ω-amino groups of diamino carboxylic acids) can be used for chemical coupling of a marker group thereto based on "amino chemistry". Well-known examples of amino chemistry comprise amongst others the reaction of amino groups with so-called activated groups, like NHS-esters, other activated esters, acid chlorides and azides.

Carboxyl groups on biomolecules (the terminal $COO^-$-group, the carboxy functions of glutamic acid or aspartic acid) are used for chemical coupling based on "carboxy chemistry". Well-known examples of carboxy chemistry comprise amongst others the activation of these of carboxy groups to carry the above mentioned activated groups. Coupling to e.g., amino groups on the marker is then easily performed.

Alternatively sulfhydryl groups on biomolecules (e.g. free-SH-groups of cysteine or —SH groups obtained by reducing di-sulfhydryl bridges) are used for chemical coupling based on "sulfhydryl chemistry". Well-known examples of sulfhydryl chemistry comprise amongst others the reaction of —SH groups with maleimido groups, or alkylation with α-halogen carboxylic group or by thioethers.

The hydroxyl group of tyrosine residues or the imidazol group of histidine also may be used to covalent link compounds according to the present invention to a biomolecule by aid, e.g., of diazonium groups.

The coupling group may be either part of the light emitting group precursor or of the leaving group precursor. It is generally accepted that large biomolecules may interfere with the luminescence light emitted by the chemiluminescent group if both the chemiluminescent group and biomolecule are in close proximity. It is therefore preferred that the coupling group is part of the leaving group precursor and to preferably use such compound for coupling to a biomolecule. In this case upon oxidation of the precursor of the leaving group the light emitting moiety precursor is released from the biomolecule and both molecules no longer are in close proximity. This is advantageous in an assay for detection of an analyte in a sample.

In general, compounds according to the invention are synthesized by reacting an activated form of the light emitting precursor, preferably an acid chloride, with the leaving group precursor in its reduced form. Chemical substances suitable as leaving group precursors like substituted anilines or phenols are commercially available or can be synthesized according to standard procedures. Leukodyes, i.e., leaving group precursors, can be obtained from commercially available dyes by reduction, preferably by reduction with sodium dithionit. Dye compounds already comprising a coupling group are suitable partners for synthesis of the inventive compounds in case the coupling group shall be attached to the leaving group precursor. For example, NHS-ester of oxazine dyes, are commercially available (e.g., Evoblue) or described in the literature (EP 0 510 668)

The term "biomolecule" comprises molecules and substances of interest in a therapeutic or a diagnostic field. Biomolecule in the sense of the present invention may be any naturally occurring or synthetically produced molecule composed of biological molecules like amino acids, nucleotides, nucleosides, lipids, and/or sugars. Non-naturally occurring derivatives thereof like artificial amino acids or artificial nucleotides or nucleic acids analogs may also be used to substitute for the biomolecule.

In a preferred embodiment the biomolecule is selected from the group consisting of polypeptides, nucleic acids, and low molecular weight drugs.

A conjugate between a biomolecule and a chemical compound comprising a light emitting moiety precursor and a precursor of a leaving group with the characteristics according to the present invention, represents a further preferred embodiment. It will be readily appreciated by the skilled artisan that conjugates between a biomolecule and the chemical compounds described in the present invention is of great advantage in a specific binding assay for detection of an analyte in a sample.

Specific binding assays in general are based on the specific interaction of two members of a bioaffine binding pair. Examples of suitable binding partners in such binding pairs are hapten or antigen and an antibody reactive thereto, biotin or biotin-analogs such as amino, biotin, iminobiotin, or desthiobiotin which binds to biotin or streptavidin, sugar and lectin nucleic acid or nucleic acid analogs and complementary nucleic acid, receptor and ligand for example steroid hormone receptor and steroid hormone, and enzymes and their substrates.

The specific interaction between nucleic acids (or nucleic acid analogs) and nucleic acids complementary thereto in assays based on detection of hybridization between nucleic acid stands and the specific interaction of antibodies with their respective antigen on which the broad range of immunoassays is based, represent the most preferred binding pairs.

The theory and practice of nucleic acids hybridization assays is summarized in relevant text books, like C. Kessler, "Non-radioactive labeling and detection of biomolecules", Springer Verlag, Berlin Heidelberg (1992). The skilled artisan will find all relevant details therein.

Immunoassays nowadays are broadly used and general knowledge to the skilled artisan. Relevant methods and procedures are summarized in related text books, like "Bioconjugation" Aslam, M. and Dent, A. (1998) 216-363, London, McMillan Reference and "Practice and theory of enzyme immunoassays" Tijssen (1990), Amsterdam, Elsevier. A comprehensive review can also be found in an article authored by Mayer, A. and Neuenhofer, S. "Angewandte Chem. Intern. Ed. Engl." (1994) 1063-1068, Weinheim, VCH Verlagsgesellschaft mbH.

The chemical compounds as described herein have the striking feature that the amide or ester bond between a light emitting moiety precursor and a precursor of a leaving group becomes unstable upon oxidation of the leaving group precursor. Light generation i.e. chemiluminescence thus is dependent on the presence of oxidants and peroxide. It therefore is evident that the chemical compounds described can be used both in assays for detection of peroxide on the one hand as well as in assays for detection of peroxidase on the other hand.

In a preferred embodiment the compounds according to the present invention are used in a method for detection of peroxide.

Peroxidase may be used to oxidize the leaving group precursor which after oxidation functions as leaving group. Under appropriate assay conditions the presence of peroxidase thus can be detected upon measurement of chemiluminescent light emitted. In a preferred embodiment the chemical compounds according to the present invention are used in a detection method based on the activity of peroxidase. Most preferred the novel compounds are used for detection of peroxidase.

In a further preferred embodiment the present invention relates to a method of performing a luminescence measurement based on the use of a compound according to the present invention. The method is characterized in that in the presence of peroxide the leaving group precursor is oxidized, the light emitting group precursor is activated, energy is emitted and measured.

The chemical compounds according to the present invention do not comprise an active leaving group. The leaving group precursor has to be oxidized and its oxidized form works as a leaving group. Oxidation refers to the oxidative step transforming the leaving group precursor into the leaving group. In case of donor-pi-donor leaving groups this means that redox processes according to the Wurster or Weitz type occur (Huenig, supra).

Various mechanisms are at hand to oxidize the aromatic system of the leaving group precursor. Dependent on the oxidizability of the leaving group precursor on the one hand and of the mode of application on the other hand appropriate oxidants are selected.

In a preferred mode for performing a method according to the present invention the oxidation is performed using a peroxidase.

It is also preferred to use appropriate chemical oxidants. For a measurement process according of the present invention, conditions for chemical oxidation have to be chosen which ensure that no destruction of the light emitting molecule occurs (that e.g., no break of a C—C bond takes place). Typical chemical oxidants include per-borate, persulfate, DDQ (dicyano dichloro quinone), diluted $HNO_3$, $BrO_4$—, $H_2O_2$, or cerammonium IV nitrate.

In a further preferred mode, oxidation is performed by electrochemical means.

The light emitting moiety precursor is readily set free after oxidation of the leaving group precursor: Upon the action of peroxide or a reactive oxygen species like the oxygen radical anion the precursor of the light emitting moiety according to the mechanism illustrated in FIG. 1 most likely forms a dioxetane intermediate which is decarboxylated to generate an electronically excited emitter. The transition to the ground state of this emitter ensues by emission of a photon (=chemiluminescence). The energy (light) which is thereby emitted is measured according to standard procedures and with routine equipment.

As indicated, $H_2O_2$ or a reactive oxygen species like the oxygen radical anion has to be present to form the intermediate dioxetanone. $H_2O_2$ can be added directly or generated indirectly e.g. by enzymatic reaction (glucose oxidase/glucose). Reactive oxygen species are generated during the chemiluminescent reaction from oxygen or $H_2O_2$. Alternatively, a reactive oxygen species can be generated intentionally e.g. by the oxygen initiated C—C coupling (indoxyl-phosphate, U.S. Pat. No. 5,589,328).

As mentioned above the light emitting group precursor is oxidized during the light generating reaction, e.g, acridan is oxidized to acridinium. Of course the oxidation conditions must be chosen that no destruction of the light emitting molecule occurs.

Preferably the reagent used for oxidation of the LEGP is the same as the one used to transform the leaving group precursor to the leaving group. Most preferred oxidation is performed and light is generated by use of $H_2O_2$ in presence of peroxidase.

The mentioned oxidation steps, e.g., catalyzed by enzymes like POD can also be accelerated by the use of mediators or enhancers.

Mediators are redox-active compounds which facilitate the oxidation of a compound by accelerating electron transfer processes. The mediator is oxidized by the oxidant and oxidizes then the compounds according to the invention, whereby the mediator is reduced again. Typical mediators are hexocyanoferrate (II) and metal complexes like ferrocene. Other enhancers which are used in chemiluminescense reactions include chemicals like iodo-phenol or phenyl boronic acid.

The oxidation preferably is performed in the presence of an appropriate detergent, which creates a hydrophobic microenvironment around the light emitting heterocyclic ketone. This results in an increase of the chemiluminescence quantum yield since quenching due to interaction with water molecules is reduced. Additionally an appropriate fluorophor, like fluorescein can be attached covalent to the detergent or alternatively a fluorophor can be added to the reaction mixture in order to get an energy transfer from the excited heterocyclic ketone to this fluorophor.

It represents an additional attractive feature of the compounds described in the present invention that quite different reaction kinetics can be generated and compounds selected as required. This becomes evident by comparing the emission kinetics as shown in FIGS. 3 and 5. Whereas a glow type reaction kinetics (slow but long lasting reaction) is very preferred in applications like the blotting techniques the flash type reactions (fast and high intensity peaks) are much preferred in liquid phase assay systems, e.g. in immunoassays. Use of a glow type compounds according to the present for staining in conjunction with a blotting technique also represents a preferred embodiment. Most preferred the flash type compounds are used in liquid phase immunoassays.

The following examples, references, and figures are provided to aid the understanding of the present invention, the true scope of which is set forth in the appended claims. It is understood that modifications can be made in the procedures set forth without departing from the spirit of the invention.

Both possible pathways are depicted. The light creating reaction, or light reaction (=LR) leads to chemiluminescence, whereas the dark reaction pathway, or dark process (DP) leads to direct hydrolysis not accompanied by light emission.

Figure 1:
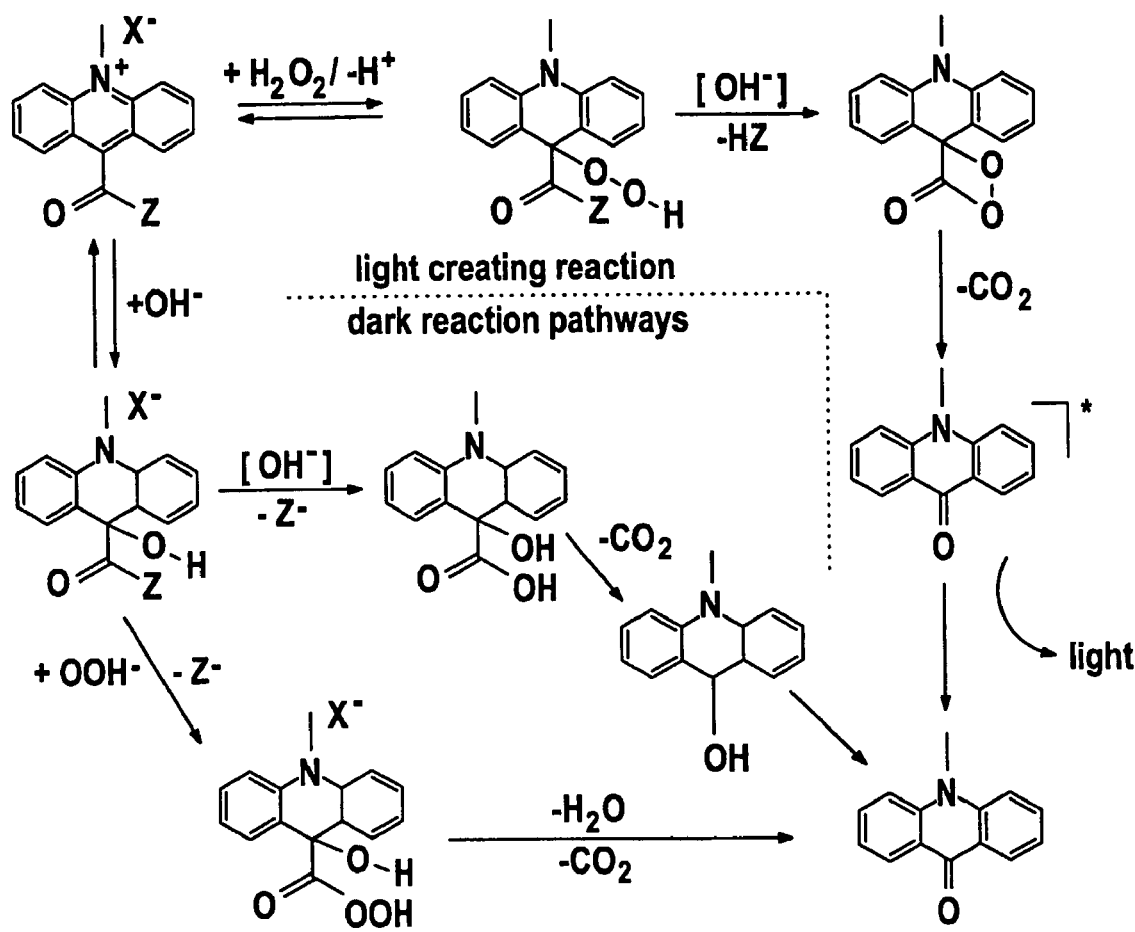
FIG. 1 Acridinium ester: Postulated reaction mechanisms
Figure 2:
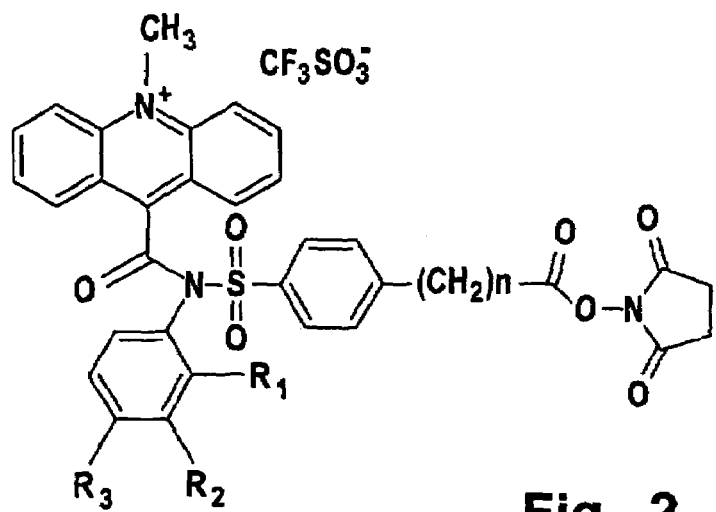

FIG. 2 Schematic of an acridinium-9-(N-sulfonyl) carboxamide label

This label 9-[aryl]-[4-(2,5-dioxo-pyrrolidin-1-yloxycarbonyl alkyl)-benzenesulfonyl]-aminocarbonyl)-10-methyl-acridinium; trifluoro-methanesulfonate, as known from the art, is depicted to illustrate a fundamental difference as compared to the compounds according to the present invention. The nitrogen atom of the amide bond is electron poor and the amide bond thus is not oxidizable under mild or moderate conditions. The sulfonyl ester leaving group of this state of the art compound represents a compromise between stability towards hydrolysis and rapid release under measurement conditions.

Figure 3:
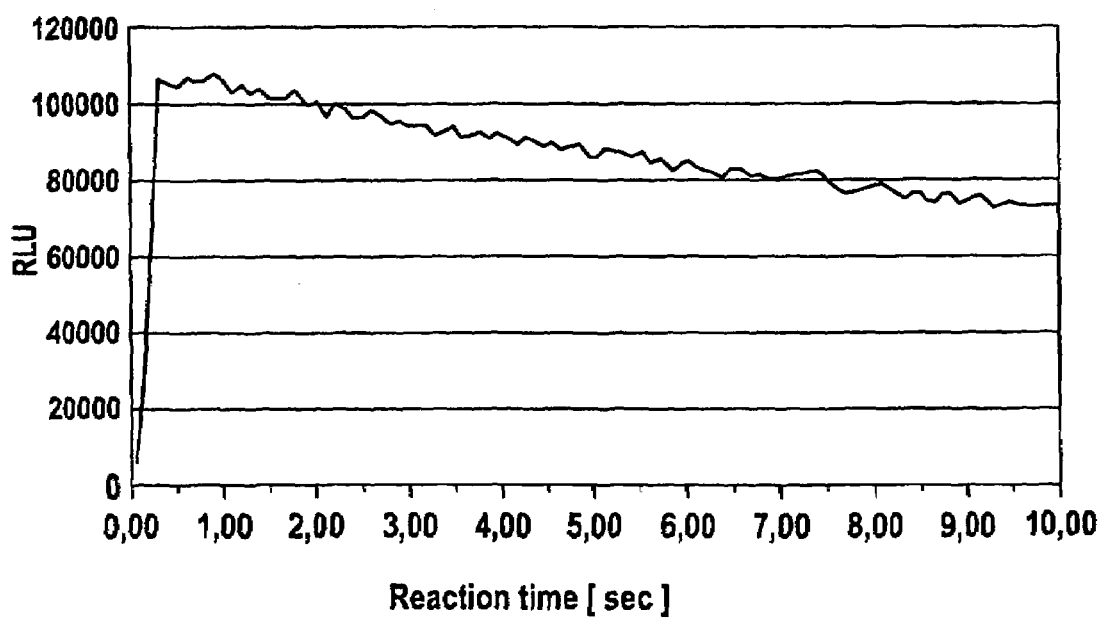

FIG. 3 Reaction kinetics of an acridinium-oxazine

This light emission (relative luminescence units=RLU) is depicted in relation to measurement time. Measurement has been performed by addition of appropriate trigger solutions as described in Example 2.

Figure 4:
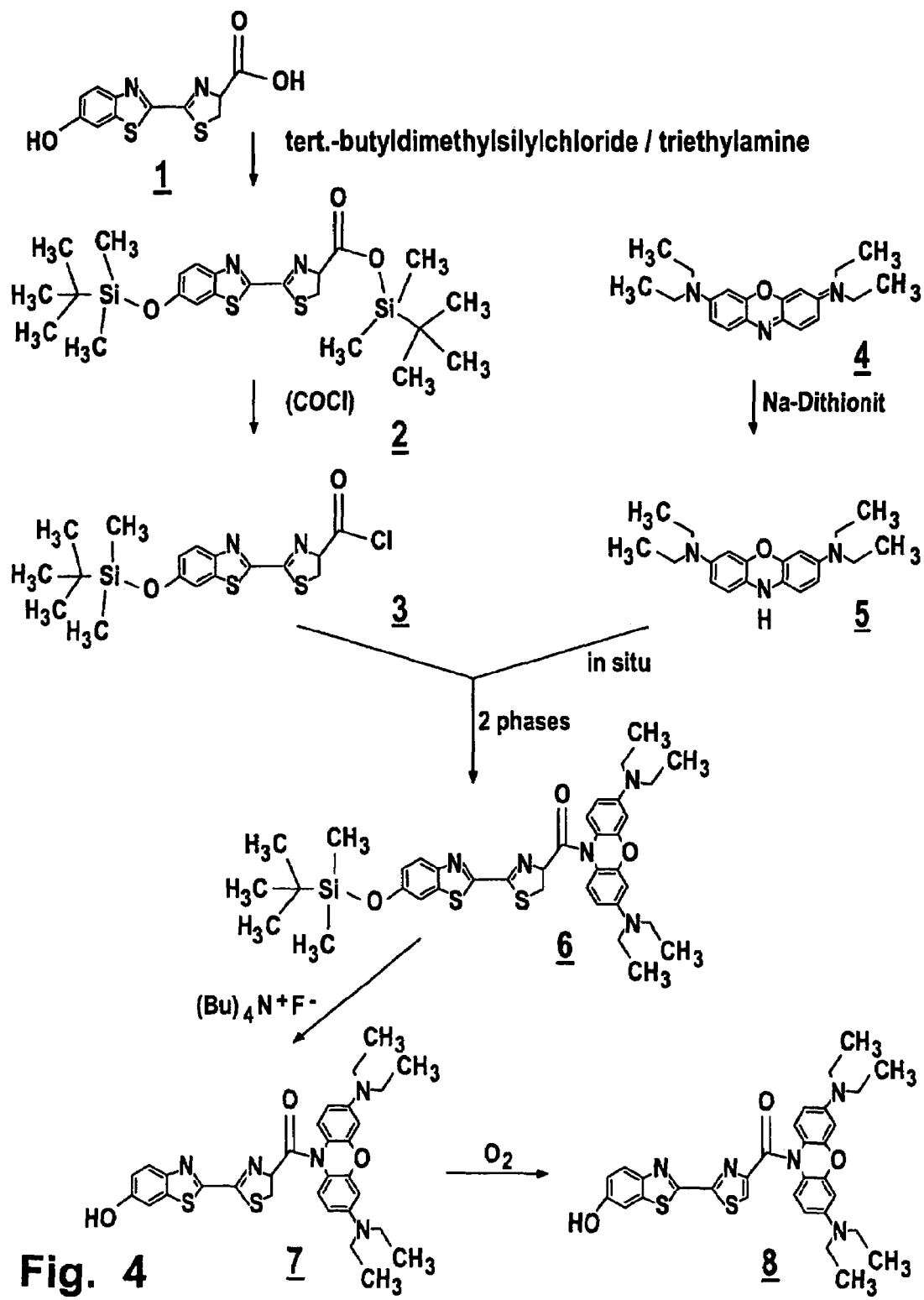

FIG. 4 Synthesis of a luciferin-oxazine

The chemical pathways used to produce (3,7-bis-diethylaminophenoxazine-10-yl)-[4,5-dihydro-2-(6-hydroxybenzothiazole-2-yl) thiazole-4-yl]-methanone (compound Z in FIG. 4) are schematically shown. Other compounds shown in this Figure are: 1=D-luciferin; 2=2-(6-tert.-butyldimethylsilyloxybenzothiazole-2-yl)-4,5-dihydro thiazole-4-yl carboxylic acid tert.-butyl dimethylsilyl ester; 3=2-(6-tert.-butyldimethylsilyloxybenzothiazole-2-yl)-4,5-dihydrothiazole-4-yl carboxylic acid chloride; 4=oxazine (3,7-bis-diethylamino-phenoxazinylium); 5=leuko-oxazine (N,N,N',N'-tetraethyl-10H-phenoxazine-3,7-diamine); 6=(3,7-bis-diethylaminophenoxazine-10-yl)-(4,5-dihydro-2-(6-tert.-butyl dimethylsilyloxy-benzothiazole-2-yl)-thiazole-4-yl)-methanone.

Figure 5:
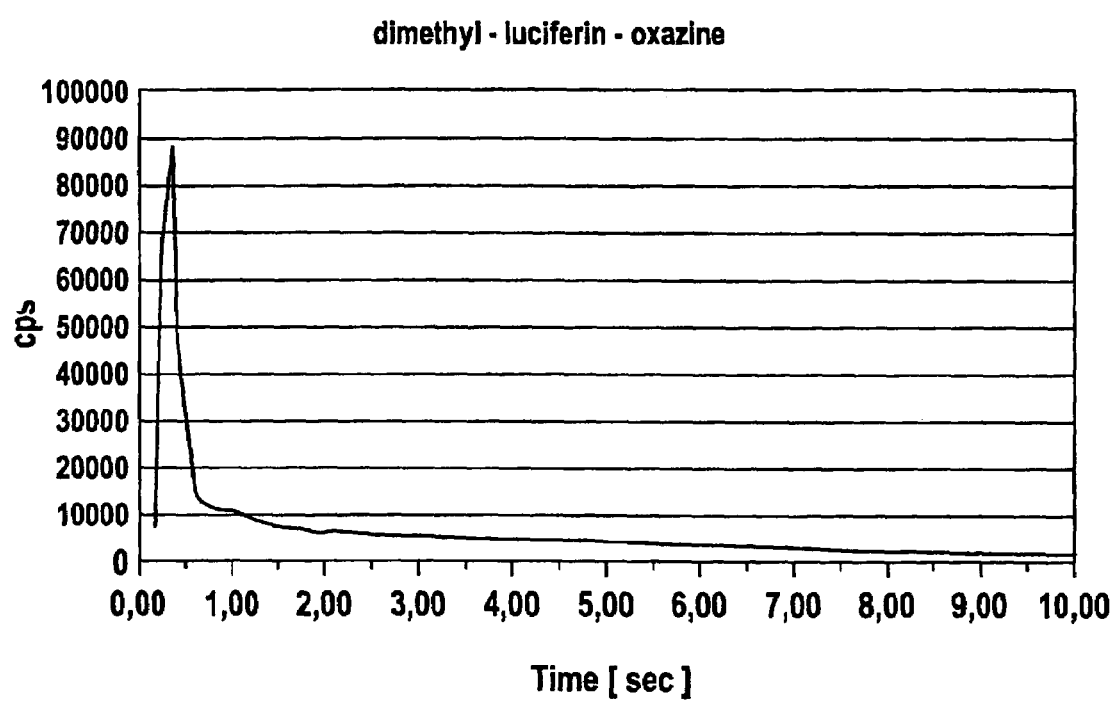

FIG. 5 Reaction kinetics of a luciferin-oxazine

Measurement has been performed as described in Example 2.

FIG. 6 Synthesis of a luciferin-benzoxazine compound

The chemical pathways for synthesis of (3,7-bis-diethylaminophenoxazin-10-yl)-[4,5-dihydro-2-(6-hydroxybenzothiazole-2-yl)-5,5-dimethylthiazole-4-yl]-methanone (structure 8 in FIG. 6) are schematically given. Other compounds shown in this Figure are: 1=2-cyano-6-hydroxybenzothiazole; 2=penicillamine; 3=dimethyl luciferin; 4=2-(6-tert.-butyldimethylsilyloxybenzothiazole-2-yl)-5,5-dimethyl-4,5-dihydro thiazole-4-yl carboxylic acid tert.-butyl dimethylsilyl ester; 5=2-(6-tert.-butyldimethylsilyloxybenzothiazole-2-yl)-5,5-dimethyl-4,5-dihydro thiazole-4-yl carboxylic acid chloride; 6=oxazine-(3,7-bis-diethylaminophenoxazinylium); 7=leuko-oxazine (N,N,N',N'-tetraethyl-10H-phenoxazine-3,7-diamine).

Figure 7:
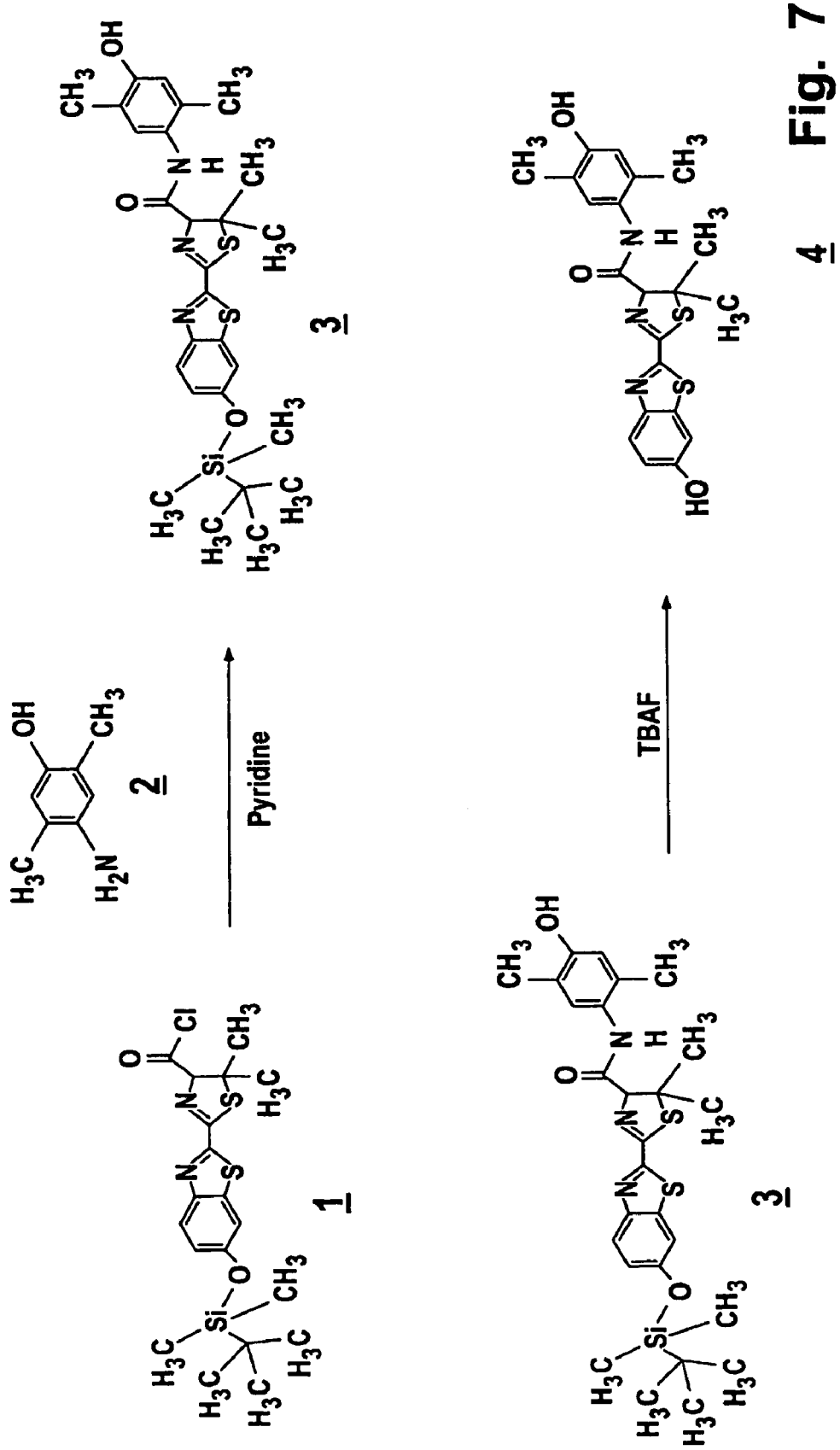

FIG. 7 Synthesis of a luciferin-anilide compound

The chemical pathways for synthesis of [4,5-Dihydro-2-(6-hydroxybenzothiazole-2-yl)-5,5-dimethylthiazole-4-yl]-carboxylic acid-2,5-dimethyl-4-hydroxyphenylamide (4 in FIG. 7) are given. Other compounds depicted are 2-(6-tert.-butyldimethylsilyloxybenzothiazole-2-yl)-4,5-dihydro-5,5-dimethylthiazole-4-yl carboxylic acid chloride 1,4-amino-2,5-dimethylphenol 2, and 2-(6-tert.-butyldimethylsilyloxybenzothiazole-2-yl)-4,5-dihydro-5,5-dimethylthiazole-4-yl-carboxylic acid-2,5-dimethyl-4-hydroxyphenylamide 3.

EXAMPLES

Example 1

Synthesis of a Compound Comprising an Acridinium-(9-carboxylic acid) as Light Emitting Group Precursor and an Oxazine as a Leaving Group Precursor a) Synthesis of acridinium-(9-carboxylic acid) Chloride 600 mg acridinium-9-carboxylic acid hydrate (Aldrich order number 24,634-4) was evaporated at 3 mbar/60° C. for 3 h. The dried residue was mixed with 5.0 ml thionyl chloride and refluxed for 3 h. The thionyl chloride was removed by distillation. The remaining (approximately 570 mg) carboxylic acid chloride was used without further purification.

b) Synthesis of (3,7-bis-diethylamino-phenoxazine-10-yl)-acridinium-9-yl-methanone Under argon atmosphere 500 mg of oxazine perchlorate (Kodak 11885) were dissolved in 80 ml degassed argon saturated water. Sodium dithionite (Merck 6507) was added until the solution was decolorized. Then a solution of 570 mg acridinium-9-carboxylic acid chloride in 80 ml was added. The mixture was vigorously stirred for 30 min. 100 ml of dest. water and 100 ml methylenchloride were added. The mixture was transferred into a separation funnel. The organic layer was separated. and washed two times with water. After drying with sodium sulfate and filtration the solvent was evaporated. The residue was dissolved in a mixture of hexanel ethyl acetate 6:4 (in a ratio of 6:4) and purified by column chromatography on silica gel 60 (Merck 1.09385.9025): Length 30 cm height 50 cm/diameter 2.5 cm: eluent: hexanelethyl acetate 6:4. The eluate was fractionated in 20 ml portions. The fractions were analyzed by TLC (thin layer chromatography) (Silica gel 60 F254 Merck 1.05735; hexanelethyl acetate 6:4). Fractions containing the desired product (in this experiment the product had an Rf value of 0.45) were collected. The solvent was removed by evaporation.

Yield: 314 mg.

c) Synthesis of (3,7-bis-diethylamino-phenoxazine-10-yl)-N-methyl acridinium-9-yl-methanone Under Argon 67 µl (0.59 mmol) of trifluoromethane sulfonic acid were added to a solution of 314 mg (0.59 mmol) (3,7-bis-diethylaminophenoxazine-10-yl)-acridinium-9-yl-methanone in 50 ml dry methylenchoride. The mixture was stirred for 16 h at room temperature. 200 ml petrolether were added, which results in precipitation of the desired product. The precipitate was filtered of by vacuum filtration and washed with petrolether. The slightly green crystals were dissolved in water and filtered by using a syringe and a filter (0.45 µm. Minisart RC 15 Sartorius 17762) The filtrate was lyophilized. The lyophilisate was dissolved in ethyl acetate and analyzed by TLC (thin layer chromatography) (Silica gel 60 F254 Merck 1.05735; hexane/ethyl acetate 6:4). The product had an Rf value of 0.41. Identy of acridinium oxazin (3,7-bis-diethylaminophenoxazine-10-yl)-N-methyl acridinium-9-yl-methanone) (M+=545.36) was confirmed by MALDI TOF MS (matrix assisted laser desorption ionization time of flight mass spectroscopy) positive mode.

Example 2

Evaluation of an Acridinium Oxazine: Kinetics, Sensitivity Quantum Yield

Measurements were performed on a Berthold Lumat LB953. To produce chemiluminescense two triggers have been used. Trigger 1 brings about the oxidation of the leaving group precursor, trigger 2 promotes chemiluminescense.

Trigger 1: 300 µl, 0.5% $H_2O_2$, 0.1M HNO3
Trigger 2: 300 µl, 0.25M NaOH

Acridinium-oxazine according to example 1 was diluted to $1 \times 10^{-8}$ Mol/l in PBS-buffer containing 0.1% Thesit. 100 µl sample was dispensed into a 5 ml-Sarstedt tube and set into the instrument. Trigger 1 was added in position −1, trigger 2 in the measuring position of the instrument. Measurement was performed for 10 sec.

The kinetics of light emission for this compound under the above conditions is depicted in FIG. 3.

Sensitivity, Quantum Yield:

A serial dilution of acridinium-oxazine in PBS-buffer containing 0.1% Thesit was performed. Each sample was measured as described above, except for the measuring time which was only 2 sec. The smallest signal still significantly different from the blank was considered as the lower detection limit.

Lower detection limit: $1 \times 10^{-11}$ Mol/l

From the maximum of signal and the amount of dye used the yield of light for this experiment was calculated to be 1.34×10e16RLU/mol.

Example 3

Synthesis of D-luciferin-oxazine (Compound 7 in FIG. 4) (3,7-bis-diethylaminophenoxazine-10-yl)-[4,5-dihydro-2-(6-hydroxybenzothiazole-2-yl) thiazole-4-yl]-methanone a) Synthesis of 2-(6-tert.-butyldimethylsilyloxybenzothiazole-2-yl)-4,5 dihydro thiazole-4-yl Carboxylic Acid Chloride (compound 3 in FIG. 4)

700 mg (2.5 mmol) D-luciferin (Sigma, no. L 9504) are dissolved in 50 ml tetrahydrofurane under argon. 830 mg (5.5 mmol) tert.-butyldimethylsilylchloride (Aldrich, no. 19,050-0) and subsequently 1.37 ml (10 mmol) triethyl amine are added at ambient temperature. After few minutes a white precipitate of ammonium chloride forms. The solution is stirred under argon overnight, then the precipitate is filtered off and the solvent removed at a rotavapor (water bath 40° C.).

The residue is dissolved in 15 ml methylene chloride, the clear solution is cooled to −15° C. and a mixture of 0.325 ml (3.75 mmol) oxalyl chloride and 10 drops of freshly destilled dimethyl formamide are added slowly over a period of several minutes under argon and vigorous stirring. Slight gas emission can be observed during this step. The reaction mixture is stirred for additional 15 minutes at −15° C., then 85 ml freshly distilled methylene chloride are added.

The resulting clear solution of acid chloride (3 in FIG. 4) is used for further reaction without purification.

b) Synthesis of (3,7-bis-diethylaminophenoxazine-10-yl)-(4,5-dihydro-2-(6-tert.-butyl dimethylsilyloxybenzothiazole-2-yl)-thiazole-4-yl)-methanone (compound 6 in FIG. 4)

0.53 g (1.25 mmol) oxazine perchlorate (Aldrich, no. 37,009-6) are dissolved in 100 distilled water and saturated with argon. Under a continuing stream of argon 1.5 g sodium dithionite are added to the dark blue solution and the reaction vessel is sealed again. After some minutes the solution turns colorless to slightly yellow by forming a blue precipitate of reduced oxazine (compound 5 in FIG. 4).

The organic solution of acid chloride (3 in FIG. 4) is added to the suspension and the resulting mixture is stirred vigorously under argon. After several minutes the blue precipitate disappears and the mixture turns slightly yellow turbid. The reaction vessel is sealed with aluminum foil and kept under argon for further 3 hours. Then the emulsion is transferred to a separation funnel and the methylene chloride phase is collected. The aqueous phase is extracted with 100 ml methylene chloride and the combined organic fractions are finally evaporated (water bath 40° C.). The remaining crude product (1.58 g blue oil) is taken into 5 ml tetrahydrofurane and applied to a silica gel column (Kieselgel 60 from Merck, 3×20 cm). The product is eluted with petrol etherlethyl acetate 4/1 (v/v), the appropriate fractions are collected and pooled. The solvent is removed and about 760 mg enriched product is obtained, which is rechromatographed on the same system.

Finally 140 mg (16%) of silylated conjugate 6 remains as slightly brownish yellow oil.

TLC (Kieselgel 60 F254, petrol ether/ethyl acetate 4/1): Rf=0.35 c) Synthesis of (3,7-bis-diethylaminophenoxazine-10-yl)-[4,5-dihydro-2-(6-hydroxybenzothiazole-2-yl)-thiazole-4-yl]-methanone (Compound 7 in FIG. 4)

140 mg (0.2 mmol) of silylated conjugate (6 in FIG. 4) are dissolved in 12 ml freshly distilled tetrahydrofurane. The solution is saturated with argon and 104.6 mg (0.4 mmol) tetrabutyl ammonium fluoride monohydrat (Aldrich, no. 24,151-2) are added. After stirring for 1 h under argon at ambient temperature 20 ml methylene chloride are added. The mixture is washed with 20 ml 5% ammonium chloride solution and subsequently 20 ml saturated bicarbonate solution. The organic phase is dried with sodium sulfate and evaporated. The highly viscous residue is dissolved in a small volume of methylene chloride and applied to a silica gel column (Kieselgel H 60, 1.5×35 cm). Separation of desired product from co-forming thiazole (8 in FIG. 4) (slightly behind) is performed with petrol ether/ethyl acetate 1/1 (v/v). Product containing fractions are pooled and evaporated. The pure conjugate (7 in FIG. 4) remains as viscous, nearly colorless oil after drying at low pressure.

TLC (Kieselgel 60 F254, petrol ether/ethyl acetate 1/1): Rf=0.60

Luminescense measurement is performed as described in Example 2.

Example 4

Synthesis of (3,7-bis-diethylaminophenoxazine-10-yl)-[4,5-dihydro-2-(6-hydroxybenzothiazole-2-yl)-5,5-dimethylthiazole-4-yl]-methanone (Structure 8 in FIG. 6)

a) Preparation of dimethylluciferin, (4,5-dihydro-2-(6-hydroxybenzothiazole-2-yl)-5,5-dimethylthiazole-4-yl carboxylic acid) (Structure 3 in FIG. 6)

704 mg (4 mmol) 2-cyano-6-hydroxybenzothiazole 1 (prepared according to EP 0024525), 596 mg (4 mmol) D-penicillanine 2 (Aldrich, no. P40-3) and 276 mg (2 mmol) potassium carbonate are dissolved in 6 ml methanol and 3.2 ml distilled water under argon atmosphere. While stirring the mixture is refluxed for 3 h to obtain a clear yellow liquid.

By using a rotary evaporator the solvents were removed at reduced pressure (water bath 40° C.). The remaining yellow brownish suspension is taken up in 100 ml distilled water and pH is adjusted to 2 with conc. hydrochloric acid. The desired product precipitates and is filtered off using a sintered glass funnel. The residue is rinsed out into a flask with a small volume of methanol. Subsequently the methanol is removed by using a rotary evaporator under reduced pressure (water bath 40° C.) to obtain a yellow solid.

TLC (Kieselgel 60 F254, methanol/chloroform 1/1): Rf=0.81 b) Preparation of 2-(6-tert.-butyldimethylsilyloxybenzothiazole-2-yl)-4,5-dihydro-5,5-dimethylthiazole-4-yl carboxylic acid chloride (Structure 5 in FIG. 6)

385 mg (1.25 mmol) dimethyl-D-luciferin 3 are dissolved in 50 ml dry tetrahydrofurane under argon atmosphere. 415 mg (2.75 mmol) tert.-butyldimethylsilyl chloride (Aldrich, no. 19,050-0) and subsequently 0,506 ml (5,0 mmol) triethyl amine are added at ambient temperature. After a few minutes a white precipitate of ammonium chloride is forming. The solution is stirred under argon atmosphere overnight, then the precipitate is filtered off and the solvent removed on a rotavapor (water bath 40° C.) to obtain 2-(6-tert.-butyldimethylsilyloxybenzothiazole-2-yl)-5,5-dimethyl-4,5-dihydro thiazole-4-yl carboxylic acid tert.-butyl dimethylsilyl ester (structure 4 in FIG. 6) as a yellow slightly brownish oil.

2-(6-tert.-butyldimethylsilyloxybenzothiazole-2-yl)-4,5-dihydro-5,5-dimethyl-4-thiazole carboxylic acid is dissolved under argon atmosphere in 8 ml dry methylene chloride, the clear solution is cooled to −15° C. and a mixture of 0.162 ml (1,875 mmol) oxalyl chloride and 500 µl of freshly distilled dimethyl formamide are added dropwise to the reaction under vigorous stirring. Slight gas emission can be observed during this step. The reaction mixture is stirred for additional 30 minutes at −15° C. and subsequently diluted with freshly destilled methylene chloride to a final volume of 30 ml.

The resulting clear solution of 2-(6-tert.-butyldimethylsilyloxybenzothiazole-2-yl)-4,5-dihydro-5,5-dimethyl-4-thiazole carboxylic acid chloride (structure 5 in FIG. 6) is directly used in the next step without further purification.

c) Preparation of (3,7-bis-diethylaminophenoxazine-10-yl)-[4,5-dihydro-2-(6-hydroxybenzothiazole-2-yl)-5,5-dimethylthiazole-4-yl]-methanone (Structure 8 in FIG. 6)

265 mg (0,625 mmol) oxazine perchlorate (structure 6 in FIG. 6) (Aldrich, no. 37,009-6) is dissolved in 50 ml distilled water and saturated with argon. Under a continuous stream of argon 30 ml pyridine and 30 ml methylene chloride are added. Additional 0.75 g sodium dithionite is given to the dark blue solution and the reaction vessel is sealed again. After a few minutes the formed two-phase reaction mixture turns colorless.

Meanwhile the acid chloride solution 5 is placed in a second flask under argon atmosphere.

The organic layer (containing leuko-oxazine (structure 7 in FIG. 6)) is transferred via thin rubber tube (standard HPLC equipment) into the second flask using high argon-pressure. The resulting reaction mixture is stirred overnight at ambient temperature to give a blue green solution.

After stripping off the solvent the remaining crude product is taken up with 5 ml tetrahydrofurane and applied to a silica gel column (silica gel 60 from Merck, 4.5×25 cm). The product is eluted with petrol ether/ethyl acetate 1/1 (v/v), the appropriate fractions are collected and pooled. The solvent is removed and about 52 mg enriched product are obtained as a deep blue green crystalline solid.

The product is dissolved in 8 ml acetonitrile/ethyl acetate 1/1 (v/v) and purified by preparative reversed phase HPLC (Waters Delta Pak C-18 column, 100 Å, 15 μm, 50×300 mm). The product is eluted with an acetonitril/distilled water gradient (0-60% acetonitrile; 0.1% trifluoro acetic acid). The appropriate fractions are collected and pooled. Finally the solvent is removed by lyophilisation to obtain 1.8 mg slightly green product (8 in FIG. 6).

TLC (Kieselgel 60 F254, petrol ether/ethyl acetate 1/1): Rf=0.44

Example 7

Synthesis of dimethy-D-luciferin-2,5-dimethyl-4-hydroxyanilide 4

[4,5-Dihydro-2-(6-hydroxybenzothiazole-2-yl)-5,5-dimethylthiazole-4-yl]-carboxylic acid-2,5-dimethyl-4-hydroxyphenylamide (4 in FIG. 7)

a) Synthesis of 2-(6-tert.-butyldimethylsilyloxybenzothiazole-2-yl)-4,5-dihydro-5,5-di-methylthiazole-4-yl-carboxylic acid-2,5-dimethyl-4-hydroxyphenylamide 3

The red brownish solution of the dimethyl-D-luciferin acid chloride of example 4b) (1 in FIG. 7) is triturated with 412 mg (3 mmol) 4-amino-2,5-dimethylphenol (2 in FIG. 7) (Aldrich, no.12,649-7) in 10 ml dry pyridine/dimethylformamide 1:1 (v/v) at −15° C. The reaction mixture is allowed to come to room temperature and stirred for an other 2 h. The solvent is evaporated, and the remaining brown oil is dried at room temperature under oil pump vacuum. About 760 mg of crude product is obtained, which is purified by preparative HPLC (Waters Delta-Pak C-18; 100 Å; 50×300 mm; 15 μm; Eluent A: 60% $H_2O$/40% Acetonitril+0.1% TFA; eluent B: 100% Acetonitril+0.1% TFA; 0->100% B in 150 min). The appropriate fractions are pooled and lyophilized.

95 mg of colorless powder are obtained.

TLC (Kieselgel 60 $F_{254}$, petrol ether/ethyl acetat 1/1 v/v): $R_f$=0.93 b) Synthesis of 4,5-Dihydro-2-(6-hydroxybenzothiazole-2-yl)-5,5-dimethylthiazole-4-yl-carboxylic acid-2,5-dimethyl-4-hydroxyphenylamide (4 in FIG. 7)

30 mg of O-protected anilide (3 in FIG. 7) are dissolved in 3 ml dry THF and 26.15 mg (0.1 mmol) tetrabutylammonium fluoride monohydrate (TBAF; Aldrich, no. 24,151-2) in 1 ml THF added to the dear orange solution while stirring under Argon atmosphere. The color changes to a deep red and after 10 min 20 ml of dichloromethane are added. The reaction mixture is washed with 2×10 ml 5% ammoniumchloride and 2× saturated bicarbonate. The organic solution is dried with a small amount of anhydrous sodium sulfat, and subsequently the solvent is removed at a rotavapor.

The product is isolated from the deep brownish mixture by preparative HPLC (Waters Delta-Pak C-18; 100 Å; 50×300 mm; 15 μm; Eluent A: 80% $H_2O$/20% Acetonitril+0.1% TFA; eluent B: 100% Acetonitril+0.1% TFA; 0->80% B in 80 min).

Fractions containing pure product (4 in FIG. 7) are pooled and lyophilized, yielding 1.95 mg orange powder.

TLC (Kieselgel 60 $F_{254}$, petrol ether/ethyl acetat 1/1 v/v): $R_f$=0.55

LIST OF REFERENCES

Huenig S., Pure Appl Chem, 62 (1990) 395-406
C. Kessler, "Non-radioactive labeling and detection of biomolecules", Springer Verlag, Berlin Heidelberg (1992)
"Methods in Enzymology" Colowick, S. P. and Caplan, N. O. (1980-1986) Academic Press
"Practice and theory of enzyme immunoassays" Tijssen (1990) Elsevier, Amsterdam
Mayer, A. and Neuenhofer, S. "Angewandte Chem. Intern. Ed. Engl." (1994) 1044-1072, Weinheim, VCH Verlagsgesellschaft mbH
Waldrop III, A. A., et al., Luminescence 15 (2000) 169-182
"Bioconjugation" Aslam, M. and Dent, A. (1998) 216-363, London, McMillan Reference
EP0 510 668
EP 625 510
U.S. Pat. No. 5,589,328
U.S. Pat. No. 5,593,845
U.S. Pat. No. 5,669,819
WO 98/56765
WO 95/19976
WO 97/33884
WO 01/09372

The invention claimed is:

1. A chemical compound comprising a light emitting moiety precursor selected from the group consisting of 2-(4 hydroxyphenyl) 4H benzo[e][1,3] oxazine-4-carboxylic acid, 2-(4-hydroxyphenyl) 4,5 dihydro thiazole 5,5 dimethyl-4-carboxylic acid, luciferin and acridinium-9-carboxylic acid and a leaving group precursor selected from the group consisting of leuko-resorufin and leuko-oxazine, wherein the carbonyl group of the light emitting precursor is linked via an amide bond to a nitrogen atom of the leaving group precursor and wherein said nitrogen atom of the leaving group precursor is an oxidizable nitrogen and part of a donor-pi-donor redox system.

2. The compound of claim 1 wherein the light emitting moiety precursor is luciferin.

3. The compound of claim 1, wherein the leaving group precursor further comprises a coupling group.

4. A conjugate comprising a biomolecule selected from the group consisting of polypeptides, nucleic acids, and drugs and a compound according to claim 1 wherein the biomolecule is linked to the compound via the coupling group.

* * * * *